United States Patent [19]

Vertesy et al.

[11] Patent Number: 5,475,094
[45] Date of Patent: Dec. 12, 1995

[54] SALMYCINS, A PROCESS FOR THEIR PREPARATION AND THEIR USE AS A PHARMACEUTICAL

[75] Inventors: László Vertesy, Eppstein; Werner Aretz, Königstein; Hans-Wolfram Fehlhaber, Idstein, all of Germany; Bimal N. Ganguli, Chembur Bombay, Ind.

[73] Assignee: Hoechst Aktiengesellschaft, Frankfurt am Main, Germany

[21] Appl. No.: 288,775

[22] Filed: Aug. 11, 1994

[30] Foreign Application Priority Data

Aug. 13, 1993 [EP] European Pat. Off. ............. 93710014
Sep. 17, 1993 [EP] European Pat. Off. ............. 93115022
Nov. 16, 1993 [EP] European Pat. Off. ............. 93118511

[51] Int. Cl.$^6$ .......................... C12P 19/26; C12N 1/20; C07H 23/00; A61K 31/71
[52] U.S. Cl. ...................... 536/17.1; 435/74; 435/84; 530/317; 530/322
[58] Field of Search .................. 530/317, 322; 514/8; 536/17.1; 435/74, 84

[56] References Cited

PUBLICATIONS

Bickel, H., et al., "Uber die Isolierung und Charakterisierung der Ferrimycine A1 and A2, neuer Antibiotika der Sideromycin–Gruppe," Helvetica Chimica ACTA, 43: 2105–2118 (1960).

Huber, P., et al., "Danoxamin, der eisenbindende Teil des Sideromycin–Antibioticums Danomycin," Helvetica Chimica ACTA, 69 (86): 236–245 (1986).

European Search Report No. EP 94 11 2382, Nov. 8, 1994.

*Primary Examiner*—Herbert J. Lilling
*Attorney, Agent, or Firm*—Finnegan, Henderson, Farabow, Garrett & Dunner

[57] ABSTRACT

Salmycins, a process for their preparation and their use as a pharmaceutical Compounds of formula I,

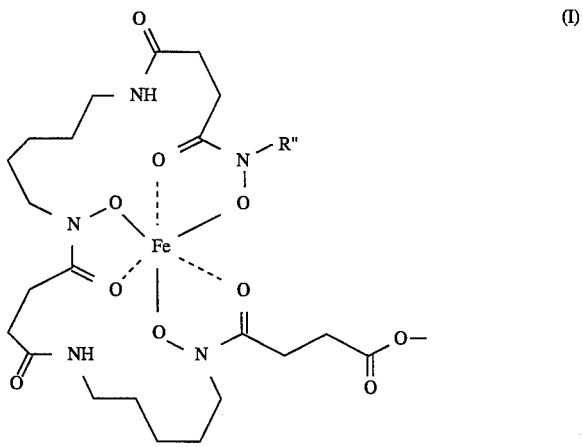

(I)

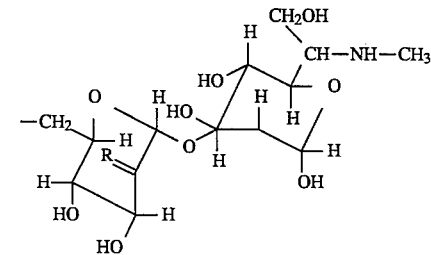

wherein R denotes =NOH (a), =O (b); —OH and —H (c), —NH$_2$ and —H (d) or =N—O—R'(e);

R' denotes phenyl or a branched or unbranched alkyl with 1 to 10 carbon atoms,

R" denotes H, alkyl, hydroxy-alkyl and amino-alkyl, as well as the chemical equivalents and physiologically acceptable salts thereof. The salmycins and their derivatives are used as a pharmaceutical.

5 Claims, No Drawings

SALMYCINS, A PROCESS FOR THEIR PREPARATION AND THEIR USE AS A PHARMACEUTICAL

The present invention relates to antibiotics, which are called salmycins, derivatives thereof, to a process for the preparation thereof and to their use as a pharmaceutical.

Known iron containing antibiotics, socalled sideromycins, are ferrimycin [M. Bickel et al., Helv. Chim. Acta 43 (1960) 2105, albomycin [G. Benz et al., Angew. Chem. 94 (1982) 552], ferrocine [B. Katayama et al., J. Antibiotics 46 (1993) 65] and danomycin [P. Huber et al., Helv. Chim. Acta 69 (1986) 236]. These antibiotics show high in vivo activities. However, they exhibit severe disadvantages. The activity of ferrocin is restricted to pseudomonas strains. Danomycin is not stable. Albomycin can be produced only in small yields.

Surprisingly, iron containing antibiotics were found, which do not exhibit the disadvantages of the known compounds and can be easily produced. The compounds according to the invention consist of an iron chelate and an amino-disaccharide-part, which is an amino-disaccharide group consisting of a keto-glucose and an amino-heptose-unit. Formula I shows the complete structure of salmycin A, B, C and D and other salmycins.

The salmycins show a high antibacterial activity, in particular against gram-positive bacteria. Since the activity mechanism of salmycins and their derivatives differs from that of conventional antibiotics, they are valuable pharmaceuticals, in particular in cases where resistances of gram-positive bacteria occur.

Accordingly, the subject of the instant invention are compounds of formula I

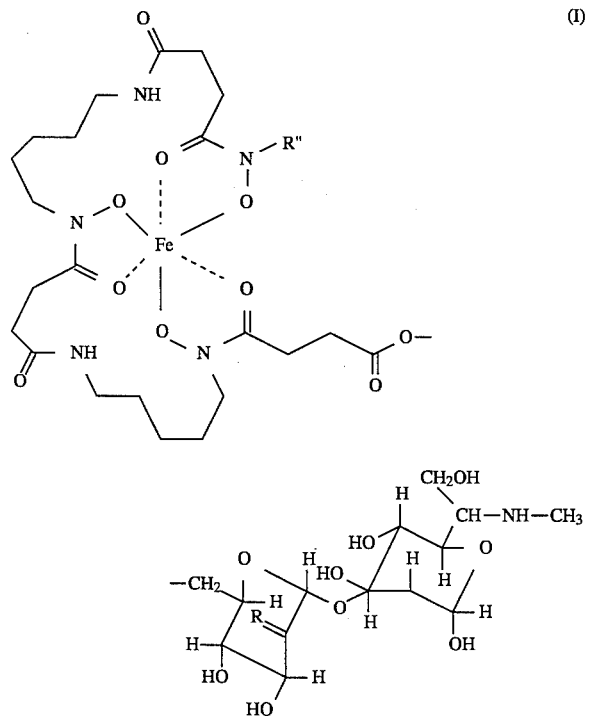

wherein

R denotes =NOH (a), =O (b); —OH and —H (c), —$NH_2$ and —H (d) or =N—O—R'(e),

R' denotes phenyl or alkyl,

R" denotes H, alkyl, hydroxy-alkyl and amino-alkyl, as well as the chemical equivalents and physiologically acceptable salts thereof.

R in formula I is either double-bonded (cases a, b and e) or stands for a single bonded substituent and a H-atom (cases c and d).

The term alkyl comprises a branched or unbranched carbon chain preferably with 1 to 10 carbon atoms. In the case of R' in formula I, the alkyl contains preferably 1 to 6 carbon atoms, in particular 1 to 3 carbon atoms. If R" in formula I contains an alkyl component, the alkyl contains preferably 3 to 6 carbon atoms, in particular 4 to 5 carbon atoms.

For the salmycins A–D—the particularly preferred compounds—the substituents have the following denotations:

salmycin A: R=NOH, R"=—$(CH_2)_5$—OH,
salmycin B: R=O, R"=—$(CH_2)_5$—OH,
salmycin C: R=O, R"=—$(CH_2)_4$—OH,
salmycin D: R=NOH, R"—$(CH_2)_4$—OH.

The term chemical equivalents and physiologically acceptable salts comprises in particular compounds which can easily be derived or are under physiologic conditions transformed into the compounds according to the instant inventions (prodrug concept). Such compounds are for instance the addition salts, such as hydrochlorides, sulfates, phosphates, acetates, citrates or the dehydrates or compounds which occur in equilibrium reactions with the compounds according to the instant invention in aequeous solution.

Furthermore the present invention relates to a process for the preparation of salmycins A, B, C and D by fermentation by means of the microorganism *streptomyces violaceus* 37290 or mutants or variants thereof and to the optional transformation of the salmycins A, B, C and D into their derivatives. The above-mentioned microorganism *streptomyces violaceus* 37290 has been deposited on May 13, 1993 with the "Deutsche Sammlung für Mikroorganismen" according to the Treaty of Budapest (DSM 8286).

Mutants and variants can be generated for instance by radiation with UV- or X-rays or by use of chemical mutagenes, e.g. ethyl-methyl-sulphonate or 2-hydroxy-4-methoxy-benzophenone. These methods are state of the art.

The culture broth for the fermentation of *streptomyces violaceus* 37290 contains a carbon and nitrogen source and the usual inorganic salts. As carbon source for instance carbohydrates or sugar alcohols like glucose, lactose or mannitol and natural products like malt extracts, oils and fats can be used. Nitrogen sources are amino acids, peptides and proteins and their metabolites like peptones and tryptones; meat extracts; milled seeds like corn, wheat, beans, soybeans or cotton seeds; distillation residues of the alcohol production; meat powder or yeast extracts; ammonium salts or nitrates.

The culture broth can contain salts like chlorides, carbonates, sulfates or phosphates and salts of the alkali or earth alkali elements and trace elements like iron, zinc, cobalt or manganese.

The production of salmycins is particularly effective in a culture broth with 0.1 to 15 weight-% nutrients, preferably in the range of 0.1 to 3 weight-%. Nutrients like soybean flour, soybean oil or mannitol can be used. Fermentation is preferably performed under aerobic conditions. The culture fluid may be aerated (air or oxygen). It may be shaken or stirred. It is preferably a submerged fermentation. The temperature range for the fermentation may be 18° to 35° C., preferably 25° to 30° C., in particular 28° to 30° C. The pH-value of the culture medium should range between pH 6 and pH 8. A pH-value between pH 6.5 and pH 7.5 is preferred. Under these conditions salmycins are generally obtained within 1 to 5 days.

It is advantageous to carry out the fermentation in several steps. A mycelium with spores can be produced by cultivation on a fluid or solid nutrient medium like yeast-malt-agar. A preculture may be formed by inoculation of a nutrient fluid and incubation for approximately 80 to 400 h. A main culture can be formed by mixing a nutrient fluid with preculture fluid, e.g. in a ratio of 1:10 volume parts. The course of fermentation can be monitored by checking the pH-value of the culture medium, the volume of the mycelium or testing of the biological activity. Mycelium and culture medium contain the produced salmycins. The main part of the product compounds is usually found in the culture fluid. The work-up may be easier, if the mycelium is separated from the fluid. This can be achieved by filtration or centrifugation.

Salmycins A–D can be isolated from the culture fluid by methods of the state of the art like adsorption, ion exchange, precipitation, reversed osmosis or chromatography. Chromatographic materials like ion exchange resins, molecular sieves, adsorption resins or reversed phases can be used. A preferred procedure for the isolation of the salmycins is adsorption on a resin. The adsorbent is preferably a styrene and divinylbenzene copolymer in a bead form, having a macroreticular structure. The adsorbent is used either in a column or a batch process. After contacting the culture fluid with the adsorbent resin, for example by passing the culture fluid over a packed column, the resin loaded with product is washed with water. The products can be eluted from the resin for example with a mixture of water and an alcohol like isopropanol. The amount of the alcohol may be increased during elution (use of a gradient).

Ultrafiltration with semi-permeable and perm-selective membranes or films can be used for concentrating and desalting of the eluted sample. Acidic by-products can be removed by treatment with an anion exchange resin (column or batch). After chromatography with molecular sieve as stationary phase a raw product is obtained, which is further separated, e.g. by reversed phase-chromatography, using $C_{18}$-silica gel or adsorption resin preferably. The procedure yields finally the solid products salmycins A, B, C and D in high purity and in high yield. The procedure is very efficient, easily performed and works very economically.

Another subject of the instant invention relates to a process for the preparation of salmycins with R″ groups different to the groups in salmycins A–D by linking together a synthetically produced siderophor and a disaccharide compound. The disaccharide component is preferably obtained from salmycin A, B, C or D.

The siderophor can be synthesized analogously to the procedure described by Prelog and Walser (Helv. Chim. Acta 45 (1962) 631) for the synthesis of ferrioxamine B and $D_1$.

In the following description of the synthesis of the siderophor compound-numbers are used, which are defined in the general reaction scheme at the end of the paragraph. The synthesis can start with R″—$NO_2$ (1), unless R″ is H. A hydoxy or amino group of the starting compound should be protected with an adequate protecting group, which is state of the art and is described in the literature (e.g. Th. W. Greene and P. G. M. Wuts, "Protective groups in organic synthesis", 2nd edition, John Wiley & Sons, New York-Chichester-Brisbane-Toronto-Singapore 1991). Common protective groups for an amino group are t-butyloxycarbonyl (BOC-group, see Greene & Wuts, page 327) or benzyloxycarbonyl (Z-group, see Greene & Wuts, page 335). Common protective groups for a hydroxy group are allyl, benzyl or substituted benzyl and silyl groups (see Greene & Wuts, pages 42, 47ff., 68ff.). The nitro group of the starting compound (1) can be reduced to the corresponding hydroxylamino-compound (2). The reduction may be performed for example with zinc dust in an ammonium chloride solution. The hydroxylamino-compound may be reacted with succinic acid, preferably in an activated form like succinic anhydride. The reaction product (3) may be treated with a dehydrating reagent like acetic anhydride or dicyclohexylcarbodiimide in order to get a 3,6-dioxo-tetrahdro-1,2-oxazine (4). This compound can be treated with 1-amino-5-nitro-pentane and the nitro-compound (5) is obtained, which may be reduced to the hydroxylamino-compound (6) and treated with succinic acid or its activated form, e.g. succinic anhydride, to get compound (7). Then preferably a 3,6-dioxo-tetrahydro-1,2-oxazine (8) is again formed, which is again treated with 1-amino-5-nitro-pentane to give compound (9). Preferably a reduction of compound (9) follows. The resulting hydroxylamino-compound (10) finally can be linked with succinic acid as described above and the desferri-form of the siderophor (11) may be obtained. If R″ stands for H the synthesis may start with hydroxylamine. The general reaction sequence is shown in the following scheme:

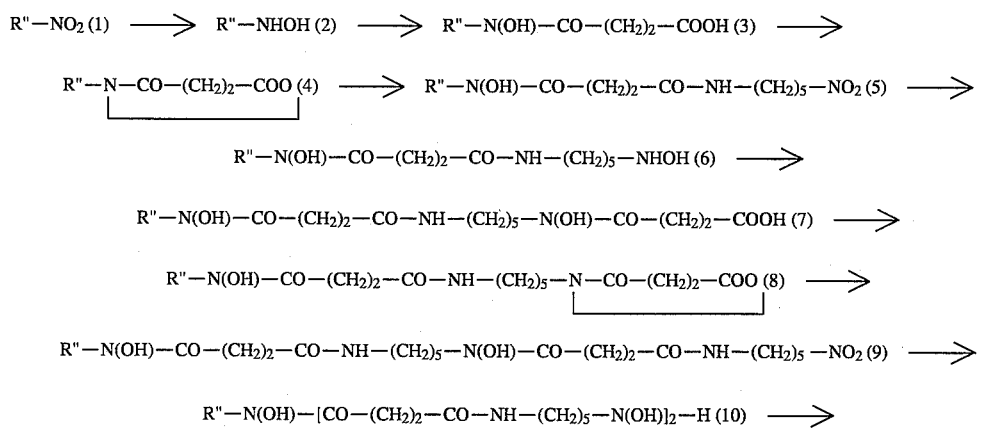

$$R'' - N(OH) - [CO - (CH_2)_2 - CO - NH - (CH_2)_5 - N(OH)]_2 - CO - (CH_2)_2 - COOH \quad (11).$$

Compound (11) can be transformed into the corresponding siderophor, preferably by treatment with an Iron-(III)-salt solution like an aqueous $FeCl_3$-solution. Protecting groups incorporated with the starting compound (1) can be removed by conventional methods (see Greene & Wuts, cited above).

The disaccharide-component used for the synthesis of salmycins may be obtained by different methods; preferably it is derived from salmycins A, B, C or D. For this purpose it may be advantageous to protect the hydroxy groups of the salmycins used as source for example with protecting groups like benzyl, substituted benzyl, silyl or allyl. The procedure of introducing such and other useful protective groups is found e.g. in Greene & Wuts (cited above). The disaccharide or its protected form is liberated by hydrolysis. The hydrolysis of salmycins A–D or their protected forms should be performed under mild conditions and can be achieved with diluted bases like ammonium hydroxide solution at room temperature preferably at pH 9.5. Usually the hydrolysis is almost complete after 2 hours. The disaccharide can be isolated by chromatography, for example reverse phase, adsorption or gel (exclusion) chromatography.

For coupling of the protected disaccharide-component with the siderophor an activation of the carboxylic group of the siderophor is helpful. Therefore the carboxylic group may be transformed into an acid chloride or may be reacted with carbodiimide, 2,6-dichloro-benzoylchloride or 2,4,6-trichlorobenzoylchloride. The obtained salmycins contain protecting groups, which can be removed by conventional methods as described in e.g. Greene & Wuts (cited above).

The coupling of the disaccharide component with a selected siderophor can also be carried out by transesterification. Salmycin A, B, C or D or their protected forms are mixed with an excess of the siderophor.

Derivatives of the salmycins, which are represented by formulae Ic–e, are preferably prepared as follows.

Hydroxy-derivative (formula Ic):

The carbonyl group of salmycins like salmycin B or C can be reduced with customary reducing agents or by cathodic reduction. The reaction is preferably carried out in aequeous solution at pH 7 with sodium borohydride ($NaBH_4$). The reduction yields two isomeric compounds. The products are separated and purified by chromatography, preferably by reversed phase chromatography with $C_{18}$-silica gel as stationary phase.

Amino-derivative (formula Id):

The carbonyl group of salmycins like salmycin B or C can be transformed into an amino group by reductive amination. Preferably the salmycin is treated in the cold with a dry solution of ammonia (maximum 17 weight-% $NH_3$ in dry methanol at room temperature) in methanol and equimolar amounts of sodium borohydride ($NaBH_4$) under stirring. The amino product is formed within a few minutes. Solvent and excess ammonia can be evaporated under reduced pressure. The product is purified by chromatography, preferably by reversed phase chromatography with $C_{18}$-silica gel as stationary phase. The obtained amino-derivative consists of two isomers.

Oxime-ether (formula Ie):

For the production of oxime-ethers of salmycins like salmycin B or C phenoxy- or alkoxy-ammonium chloride, preferably methoxy- ($CH_3ONH_3Cl$) or ethoxy-ammonium chloride ($C_2H_5ONH_3Cl$), and an aequeous solution of the salmycin are mixed. The reaction is carried out preferably in a solution of pH 7 and at room temperature for several hours. The work-up of the solution comprises concentration and desalting. The product can be purified by chromatography, preferably by reversed phase chromatography with $C_{18}$-silica gel as stationary phase. The two possible oxime-ethers are obtained for salmycin B or C respectively.

Salmycin A may also be formed by reaction of salmycin B with hydroxylamine, salmycin D by reaction of salmycin C with hydroxylamine.

A further subject of the instant invention are pharmaceuticals, containing one or more salmycin, their derivatives, chemical equivalents or physiologically tolerated salts of these substances (i.e. one or more compounds of formulae Ia–e and their physiologically tolerated salts). The pharmaceuticals can be prepared by mixing one or more of said compounds with one or more pharmacologically tolerated vehicles or diluents such as, for example, fillers, emulsifiers, lubricants, masking flavours, colerants or buffer substances, and converted into a suitable pharmaceutical form such as, for example, tablets, capsules or a suspension or solution suitable for parenteral administration.

Examples of vehicles or diluents which may be mentioned are tragacanth, lactose, talc, agar-agar, polyglycols, hydrocolloids, ethanol and water. Suitable and preferred for parenteral administration are suspension or solutions in water. It is also possible to administer the active substance as such, without vehicles or diluents, in a suitable form, e.g. in capsules.

EXAMPLES

Example 1

Culturing of *streptomyces violaceus* for the preparation of salmycins

Composition of the culture medium:

| | |
|---|---|
| Starch | 10 g/l |
| Casein | 1 g/l |
| Pepton | 1 g/l |
| Yeast extract | 1 g/l |
| Malt extract | 10 g/l |
| $K_2HPO_4$ | 0,5 g/l |
| Agar | 15 g/l |

The medium is sterilized at 121° C. for ½ hour, cooled to 45° C. and poured into Petri dishes. The Petri dishes are inoculated with a suspension of spores of *streptomyces violaceus* and incubated for 8 days at 28° C. Storage at 4° C.

1 $cm^2$ of an incubated Petri dish is used for inoculation of a preculture of 500 ml volume.

Composition of the culture fluid (preculture):

| | |
|---|---|
| Glucose | 15 g/l |
| Soybean flour | 15 g/l |
| Cornsteep liquor | 5 ml/l |
| $CaCO_3$ | 2 g/l |
| NaCl | 5 g/l |
| pH | 7.2. |

It is incubated for 2 days at 28° C. and shaken on a rotary shaker at 240 rpm. On a next stage 25 ml of the preculture fluid are used for inoculation of 50 ml nutrient fluid, filled in 500 ml Erlenmeyer flasks (main culture).

The composition of the main culture fluid is:

| | |
|---|---|
| Soybean flour | 20 g/l |
| Mannitol | 20 g/l |
| pH | 7.5. |

Incubation conditions are: 28° C., shaking on a rotary shaker at 240 rpm, 3–4 days duration. Finally a diffusion test shows a biological activity of 21–23 mm diameter of inhibition zone of *staphylococcus aureus* 209 P.

Example 2

Fermentation

The fermentation is carried out in 12 I-vessels with 9 I culture fluid (identical to main culture fluid, example 1:20 g/l soybean flour+20 g/l mannitol, pH 7.5). 90 ml of the main culture (example 1) are used for inoculation. Incubation conditions are: 28° C., shaking at 500 rpm, aeration rate of 0.5 liter per minute, 2–3 days duration.

After the fermentation is terminated the culture filtrate is tested using the agar well method. The diameter of a zone of inhibition of *staphylococcus aureus* 209 P is usually in the range of 22–27 mm.

Example 3

Isolation of raw product

180 I broth filtrate of cultures prepared according to example 2 are brought to pH 6.8 and are passed through a 17 I-column packed with an adsorbent resin. A styrene and divinylbenzene copolymer in a bead form like ®Diaion HP 20 (Mitsubishi Chem. Ind., Japan) is preferably used. The column is washed with demineralized water and is eluted with a concentration gradient of 0–20 Vol.-% isopropanol. Fractions are collected and their biological activity is tested. Fractions containing salmycines are combined (ca. 30 I overall). The solution is liberated from acidic components by passing over an anion exchange column (1 I of diethylaminoethyl-sepharose like DEAE- ®Sephadex Fast Flow from Pharmacia Fine Chemicals AB, Sweden), which was equilibrated with an ammonium acetate solution.

The sample solution is then concentrated by ultrafiltration using semi-permeable and perm-selective ®Nadir UF-CA-1-membranes (Hoechst; Frankfurt, Germany). The solvent is evaporated under reduced pressure and the residue is freeze-dried. 38 g of raw product mixture results.

Example 4

Pre-separation of raw product mixture 35 g raw product mixture prepared according to example 3 are dissolved in distilled water and passed over a 3.5 I-column (11.3 cm inner diameter; 36 cm height), which is packed with an adsorbent like "MCI-Gel CHP20P" (Mitsubishi Kasei Corp., Tokyo, Japan), based on a styrene and divinylbenzene copolymer. The column is washed with water. The products are eluted with a concentration gradient of 0–10 vol.-% isopropanol. 1 I-fractions are collected. Fractions containing a mixture of salmycin B and C and fractions mainly of salmycin A are obtained. Concentration under reduced pressure and lyophilization give 3.2 g raw mixture of salmycin B and C and 1.4 g crude salmycin A.

Example 5

Purification of salmycin B and C

The raw mixture of salmycin B and C obtained according to example 4 is passed over a column of 10 cm inner diameter and 52 cm height, filled with molecular sieve, such as ®Fractogel TSK HW-40F (E. Merck, Darmstadt, Germany), which is a hydrophilic vinyl polymer made for gel permeation chromatograpghy for fractionating low molecular compounds like dextrans in the molecular range of 100–7000 g/mol. A mixture of equal parts of water and methanol and 1 vol.-% acetic acid is used as solvent. 24 ml fractions are collected. Fractions, containing salmycin B or C, are combined and concentrated under reduced pressure. Lyophilization gives 510 mg of raw product, containing 82 weight-% salmycin B and 3 weight-% salmycin C.

Example 6

Purification of salmycin A 1.4 g crude salmycin A are purified by use of molecular sieve like in example 5. The solvent consists of 4 parts water and 1 part ethanol. Fractions containing salmycin A are combined. Concentration under reduced pressure and lyophilization give 240 mg crude salmycin A with a content of 85 weight-%.

Example 7

Final preparation of salmycin A and D

The crude salmycin A and from example 6, which contains also salmycin D, is dissolved in distilled water and purified by reversed phase chromatography. A column of 3.2 cm inner diameter and 25 cm height was packed with 200 ml octadecyl-silica gel like ®Nucleosil 12 $C_{18}$ AB (Macherey & Nagel, Düren, Germany). As solvent a water-acetonitrile-mixture is used with a concentration gradient of 0–10 vol.-% acetonitrile. 25 ml-fractions are collected. Fractions with salmycin A and D are combined respectively. Concentration under reduced pressure and lyophilization give 6 mg salmycin D and 130 mg product, containing 99% salmycin A by weight.

Characterization of salmycin A:

a) high resolution FAB-mass spectrometry: molecule ion peak of M+H$^+$:1053.4050±0,0006 dalton. mass calculated for M+H$^+$ of $C_{41}H_{70}FeN_7O_{21}$, mono-isotopic: 1053.4052 dalton.

b) $^1$H—NMR of Desferri-salmycin A: signals at 2.8 ppm in $D_2O$ (N-methyl group), no further signals for methyl-protons. $^{13}$C—NMR of Desferri-salmycin A in $D_2O$: signals (in ppm) at 25.0 (t), 25.9 (t), 28.3 (t), 28.4 (t), 29.7 (t), 30.5 (t), 30.7 (t), 31.5 (t), [33.3 (t)], 33.4 (t), 33.7 (t), 42.0 (t), 50,8 (t), 58,6 (t), 58,8 (t), 61,8 (d), 62,3 (d), 64,4 (t), 62–82 (several signals), 91.5 (d), 92.4 (d), 99.1 (d), 176.6 (s), 177.7 (s), 177.8 (s).

c) UV-vis of aqueous solution (phosphate buffer, pH 7.0): end absorption and broad absorption around 430 nm (logε=3.3).

In neutral or weak alkaline aqueous solution salmycin A is in equilibrium with another species of the same general formula, which is less polar than the chromatographiccally charactericed salmycin A. In the mass spectrum (e.g. electron spray ionisation mass spectrometry) of the equilibrium species a fragment of the mass 1035 dalton is observed (dehydration-product).

Characterization of salmycin D:

a) ESI-mass spectrometry (electron spray ionisation): molecule ion peak of M+ H$^+$:1039.4 dalton. general formula:

$C_{40}H_{68}FeN_7O_{21}$ b) $^1$H-NMR of Desferri-salmycin D: signals at 2.8 ppm in $D_2O$ (N-methyl group), no further signals for methyl-protons.

c) UV-vis of aqueous solution (phosphate buffer, pH 7.0): end absorption and broad absorption around 430 nm (log$\epsilon$=3.3).

Example 8

Final preparation of salmycin B and C

The mixture of salmycin B and C obtained according to example 5 is purified by reversed phase chromatography in a manner similar to example 7. The solvent consists of a mixture of water, 6 vol.-% acetonitrile and 0.1 vol.-% trifluoro acetic acid. 402 mg salmycin B and 8 mg salmycin C are obtained.

Characterization of salmycin B:

a) high resolution FAB-mass spectrometry:
  molecule ion peak of M+H$^+$:1038.3941±0.0007 dalton.
  mass calculated for M+H$^+$ of $C_{41}H_{69}FeN_6O_{21}$, monoisotopic: 1038.3943 dalton.
  molecule ion peak of M+H$^+$+H$_2$O:1056.406±0.001 dalton.
  mass calculated for M+H$^+$+H$_2$O:1056.4053 dalton.

b) $^1$H-NMR: signals at 2.8 ppm in D$_2$O (N-methyl group), no further signals for methyl-protons.

c) UV-vis of aqueous solution (phosphate buffer, pH 7.0): end absorption and broad absorption around 427 nm (log$\epsilon$=3.3).

Characterization of salmycin C:

a) ESI-MS-spectrometry (electron spray ionisation):
  molecular ion peak M+H$^+$:1024.4 dalton.
  molecular ion peak M+H$^+$+H$_2$O:1042.4 dalton.
  general formula: $C_{40}H_{67}FeN_6O_{21}$.

b) $^1$H-NMR: signals at 2.8 ppm in D$_2$O (N-methyl group), no further signals for methyl-protons.

c) UV-vis of aqueous solution (phosphate buffer, pH 7.0): end absorption and broad absorption around 430 nm (log$\epsilon$=3.3).

The salmycins show zones of inhibition with isolated resistant strains which are typical for sideromycins. The agar diffusion test shows antibacterial activity of the salmycins against streptococcus strains, staphylococcus strains and methicillin-resistant strains. A determination of the minimal concentration for inhibition is for said species not possible. Salmycin A shows in contrast to salmycin B and C always clear zones of inhibition. Chymotrypsin or β-lactamase do not react with the salmycins.

Example 9

Reaction of salmycin B with hydroxylamine forming salmycin A 100 mg salmycin B are dissolved in 100 ml distilled water and mixed with 100 mg hydroxyl-amine-hydrochloride. The pH-value is adjusted to pH 4.5 with phosphate buffer. Reaction time is 3 hours. The formed salmycin A is isolated as described in example 7. 87 mg salmycin A resulted, having a purity of 98 weight-%.

Example 10

Preparation of salmycin A-oxime-methylether 100 mg salmycin B are dissolved in 100 ml phosphate buffer, pH 7, and mixed with 100 mg O-methylhydroxylammonium chloride (E. Merck, Art.-Nr. 10 592). Reaction time is 5 hours. Two forms of salmycin A-oxime-methylether (syn and anti) are formed. They are isolated as described in example 7. 41 mg of the syn-form and 44 mg of the anti-form are obtained. The reaction is monitored with a HPLC-system (®Nukleosil 7-C$_{18}$ AB; Macherey & Nagel, Düren, Germany) with a mixture of water/8.75 vol.-% acetonitrile/0,1 vol.-% trifluoro acetic acid as solvent.

Example 11

Reduction products of salmycin B 104 mg salmycin B are dissolved in potassium phosphate buffer, pH 7.0, and mixed with 2 mg sodium borohydride. The reaction mixture is left at room temperature. The course of the reaction is monitored by HPLC (column: ®Nukleosil 7-C$_{18}$AB (Macherey & Nagel); solvent: water/10 vol.-% acetonitrile/0. 1 vol.-% trifluoro acetic acid). The reaction is almost completed after 2 hours. The reaction mixture is separated by preparative HPLC (column: 80 ml ®Nukleosil 10-C$_{18}$ AB (Macherey & Nagel); solvent: water/6 vol.-% acetonitrile/0.1 vol.-% trifluoro acetic acid).

Fractions are concentrated under reduced pressure and lyophilized to give 37 mg mannosyl-reduction product and 33 mg glucosyl-reduction product. These products appear as salts of trifluoro acetic acid with a purity of 97 and 95 weight- %, respectively.

Both compounds show molecular peaks M+H$^+$=1040 dalton in FAB-MS-Spectra, which corresponds to the molecular formula $C_{41}H_{71}FeN_6O_{21}$.

Example 12

Reductive amination of salmycin B 10 g of dry gaseous ammonia (NH$_3$) are passed in 100 ml dry methanol at −10° C. 100 mg salmycin B dissolved in 10 ml dry methanol and 5 mg sodium borohydride (NaBH$_4$) suspended in 5 ml methanol are added to this solution. The reaction mixture is stirred for 10 minutes. Solvent and NH$_3$ are removed under reduced pressure. The residue is purified as described in example 11. Two isomeric amino compounds are obtained, which are represented by formula Id.

Example 13

Reaction of salmycin C with hydroxylamine forming salmycin D 5 mg salmycin C are dissolved in 5 ml distilled water and mixed with 5 mg hydroxylamine-hydrochloride. The pH-value is adjusted to pH 4.5 with phosphate buffer. Reaction time is 4 hours. The formed salmycin D is isolated as described in example 7. 4.5 mg salmycin D resulted.

Example 14

Preparation of the disaccharide 100 mg salmycin A, B, C or D or a protected form thereof are dissolved in 20 ml water and the pH-value of the solution is brought to pH 9.5 by adding 0.1M NaOH-solution in drops. The hydrolysis is performed at room temperature and is almost complete after 2 hours. Afterwards the solution is neutralized. The disaccharide or its protetected form are isolated by reverse phase chromatography, e.g. by HPLC using C$_{18}$-silicagel as stationary phase and pure water as eluent.

We claim:
1. Compounds of formula I,

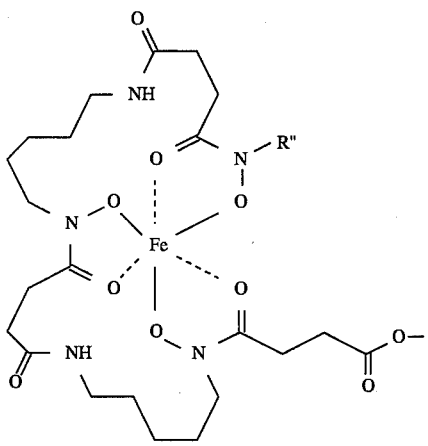

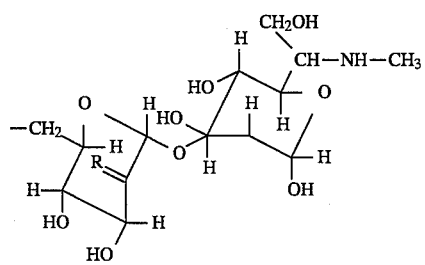

wherein

R denotes =NOH (a), =O (b); —OH and —H (c), —NH$_2$ and —H (d) or =N—O—R'(e);

R' denotes phenyl or a branched or unbranched alkyl with 1 to 10 carbon atoms,

R" denotes H, alkyl, hydroxy-alkyl and amino-alkyl, as well as the chemical equivalents and physiologically acceptable salts thereof.

2. Compounds as claimed in claim 1, wherein the substituents have the following denotations:

salmycin A: R=NOH, R"=—(CH$_2$)$_5$—OH, salmycin B: R=O, R"=—(CH$_2$)$_5$—OH, salmycin C: R=O, R"=—(CH$_2$)$_4$—OH, salmycin D: R=NOH, R"=—(CH$_2$)$_4$—OH.

3. Compounds as claimed in claim 1 as a pharmaceutical.

4. Pharmaceuticals, which contain one or more compounds as claimed in claim 1, if appropriate together with customary auxiliaries and/or vehicles.

5. A process for the preparation of pharmaceuticals as claimed in claim 4, wherein one or more of the compounds as claimed in claim 1 are brought, optionally with customary auxiliaries and/or vehicles, into a suitable form for administration.

* * * * *

UNITED STATES PATENT AND TRADEMARK OFFICE
CERTIFICATE OF CORRECTION

PATENT NO. : 5,475,094
DATED : December 12, 1995
INVENTOR(S) : VERTESY ET AL.

Page 1 of 2

It is certified that error appears in the above-indentified patent and that said Letters Patent is hereby corrected as shown below:

In the abstract and in claim 1, column 11, delete the Formula I

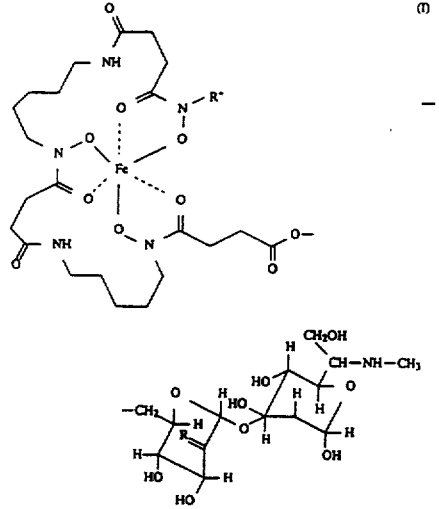

UNITED STATES PATENT AND TRADEMARK OFFICE
CERTIFICATE OF CORRECTION

PATENT NO. : 5,475,094                                    Page 2 of 2
DATED     : December 12, 1995
INVENTOR(S) : Vertesy et al.

It is certified that error appears in the above-indentified patent and that said Letters Patent is hereby corrected as shown below:

and insert therefor

-- 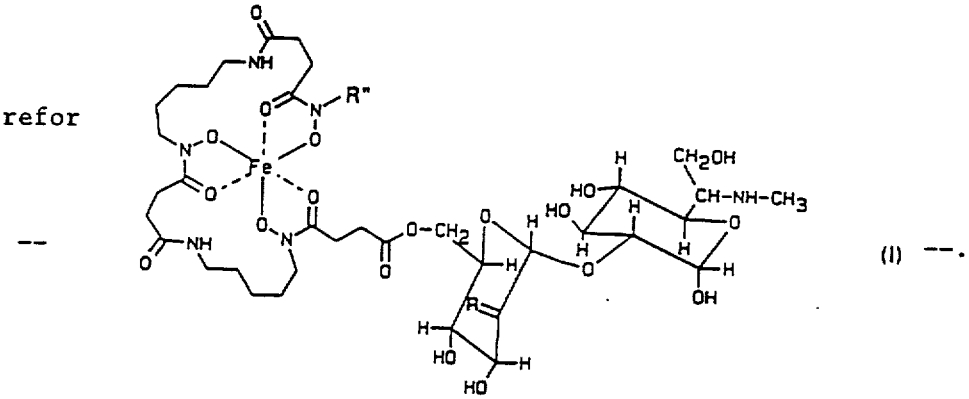 (I) --.

Signed and Sealed this

Thirteenth Day of August, 1996

Attest:

BRUCE LEHMAN

Attesting Officer                Commissioner of Patents and Trademarks